(12) United States Patent
Lee et al.

(10) Patent No.: US 7,135,294 B2
(45) Date of Patent: Nov. 14, 2006

(54) METHOD FOR DETECTING PCR PRODUCT USING ELECTRICAL SIGNAL

(75) Inventors: Jae-hoon Lee, Kyungki-do (KR); Jae-chang Lee, Kyungki-do (KR); Dae-sung Yoon, Kyungki-do (KR); Geun-bae Lim, Kyungki-do (KR)

(73) Assignee: Samsung Electronics Co., Ltd. (KR)

( * ) Notice: Subject to any disclaimer, the term of this patent is extended or adjusted under 35 U.S.C. 154(b) by 5 days.

(21) Appl. No.: 10/658,169

(22) Filed: Sep. 9, 2003

(65) Prior Publication Data

US 2004/0100284 A1    May 27, 2004

(30) Foreign Application Priority Data

Nov. 12, 2002 (KR) .................. 10-2002-0070141

(51) Int. Cl.
*C12Q 1/68* (2006.01)
*C12P 19/34* (2006.01)
*G01R 27/26* (2006.01)

(52) U.S. Cl. .................. 435/6; 435/91.2; 324/663

(58) Field of Classification Search ............... 324/558, 324/660, 661, 663; 205/775, 777.5; 204/403.01, 204/403.02, 194; 422/91.1, 91.2; 435/91.2, 435/6

See application file for complete search history.

(56) References Cited

U.S. PATENT DOCUMENTS

| | | | | |
|---|---|---|---|---|
| 4,023,096 | A | * | 5/1977 | Schmidt .................. 324/663 |
| 4,683,202 | A | * | 7/1987 | Mullis .................. 435/91.2 |
| 5,587,128 | A | * | 12/1996 | Wilding et al. ............. 422/50 |
| 6,126,899 | A | * | 10/2000 | Woudenberg et al. ......... 422/50 |
| 6,169,394 | B1 | * | 1/2001 | Frazier et al. ............. 324/71.4 |
| 6,264,825 | B1 | * | 7/2001 | Blackburn et al. ....... 205/777.5 |
| 6,686,150 | B1 | * | 2/2004 | Blackburn et al. ............ 435/6 |
| 2002/0007254 | A1 | | 1/2002 | Takeda et al. ............. 702/182 |
| 2002/0072054 | A1 | | 6/2002 | Miles et al. ................. 435/6 |
| 2002/0151039 | A1 | * | 10/2002 | Wittwer et al. .......... 435/286.1 |
| 2003/0027169 | A1 | * | 2/2003 | Zhang et al. ................ 435/6 |

FOREIGN PATENT DOCUMENTS

| | | |
|---|---|---|
| WO | WO 99/10530 | 3/1999 |
| WO | WO 01/42508 A3 | 6/2001 |
| WO | WO 01/59154 A2 | 8/2001 |
| WO | WO 01/81619 A2 | 11/2001 |

OTHER PUBLICATIONS

Elsevier; Journal of Chromatography A, 781; "Microchip-based capillary electrophoresis of human serum proteins"; Authors: Christa L. Colyer, Shakuntala D. Mangru and D. Jed Harrison; 1997; pp. 271-276.

Elsivier; Sensors and Actuators B, 83; "Design of an electronic interface for capacitively coupled four-electrode conductivity detection in capillary electrophoresis microchip"; Authors: F. Laugere, G.W. Lubking, J. Bastemeijer and M.J. Vellekoop; 2002; pp. 104-108.

Analytical Chemistry, vol. 74, No. 9; "Contactless Conductivity Detector for Micorchip Capillary Electrophoresis"; Authors: Martin Pumera, Joseph Wang, Frantisek Opekar, Ivan Jelinek, Jason Feldman, Holger Lowe and Steffen Hardt; May 1, 2002; pp. 1968-1971.

European Search Report; Application No. 03020611.4-2402; Date of Completion: Jan. 13, 2004.

* cited by examiner

*Primary Examiner*—Vincent Q. Nguyen
*Assistant Examiner*—Jeff Natalini
(74) *Attorney, Agent, or Firm*—Cantor Colburn LLP

(57) ABSTRACT

A method for detecting a polymerase chain reaction (PCR) product is provided. The method includes (a) providing at least a pair of electrodes in a PCR solution-containing vessel; (b) performing PCR; (c) producing an electric field between the electrodes; and (d) measuring a change in a dielectric property in the PCR solution. Therefore, a PCR product can be detected in real time.

2 Claims, 12 Drawing Sheets

METHOD FOR DETECTING PCR PRODUCT USING ELECTRICAL SIGNAL

BACKGROUND OF THE INVENTION

This application claims the priority of Korean Patent Application No. 2002-70141, filed on Nov. 12, 2002, in the Korean Intellectual Property Office, the disclosure of which is incorporated herein in its entirety by reference.

1. Field of the Invention

The present invention relates to a method for detecting a polymerase chain reaction (PCR) product using an electrical signal.

2. Description of the Related Art

A representative biosensor includes an enzyme sensor and an immune sensor using an immune response of the immune system. However, as a considerable amount of DNA information is obtained by the completion of the human genome project, and thus, potential and expectation of an early discovery and treatment of human genetic diseases increase, a DNA chip is rapidly emerging as another type of biosensor. Presently, active research areas in the development of biosensors are the possibilities of obtaining a low manufacturing cost, high speed, accuracy, easy handling property, and miniaturization (portability). In this regard, a DNA sensor for detecting a human disease at an early stage by using DNA information must be also developed toward satisfaction of the above requirements to strengthen an international market competitiveness.

One of essential genetic assays is a PCR DNA assay, which has been widely used in clinical, biological, and genetic laboratories since it was invented at the end of the 1980s.

A traditional PCR shows the qualitative results of amplified DNA by a gel electrophoresis at the end-point of the PCR reaction, but has many problems such as inaccuracy of the quantitative detection of DNA. Therefore, a Real-Time PCR was developed to allow for the quantitative detection of amplified DNA by detecting the intensity of fluorescent light, which is in proportional to the concentration of the amplified DNA, using an optical detection system.

A quantitative assay of DNA is essential for studies of disease treatments and DNA expression. For example, in order to ensure a successful medicinal therapy for patients infected with hepatitis B-type virus (HBV), the drug resistance of HBV must be tested by periodically detecting the concentration of HBV in the blood plasma using a Real-Time PCR.

A conventional Real-Time PCR requires many optical devices such as a laser source, a micromirror, a microscope, and a filter, and an expensive fluorescent dye. In addition, because a conventional Real-Time PCR chip is based on the principle of detecting fluorescent light, there are many disadvantages in terms of miniaturization (on a chip) and economical efficiency.

In order to solve this problem, an effort was made to electrically detect DNA using capillary electrophoresis (CE) [Christa L. Colyer et al, *Journal of Chromatography A*, Volume 781, Issues 1–2, 26 Sep. 1997, pp. 271–276; F. Laugere et al, *Sensors and Actuators B: Chemical*, Volume 83, Issues 1–3, 15 Mar. 2002, pp. 104–108; Pumera et al., *Anal. Chem.*, 2002, 74(9), pp. 1968–1971). This method allows for a qualitative assay, but has many problems for a quantitative assay. In addition, transfer of PCR products to a CE detection system using a micro-channel after the completion of PCR is a laborious process and a high voltage is required. Therefore, requirements of economical efficiency and miniaturization are not satisfied.

Miles et al. filed a U.S. patent application, which has been published under U.S. Patent Application Publication No. 2002/007254A1, based on the concept that as the concentration of DNA increases during PCR, impedance decreases and conductivity increases. However, the Miles' concept that impedance decreases as the concentration of DNA increases during PCR is contrary to the fact demonstrated by the present inventors. Therefore, this patent application comes from a misunderstanding of the mechanism of PCR reaction.

During PCR, dNTPs are dissociated into dNMPs and many diphosphates. At the same time, dNMPs are polymerized into DNA using a primer supplementary to a template DNA. In this case, the disclosure of Miles et al. considers only the electrical mobility of diphosphates as a byproduct. However, considering an entire electrical mobility which decreases by dNMPs, a primer, and a template, all of which have electric charges during DNA synthesis, as the concentration of DNA increases, impedance of PCR increases due to the decrease of the electrical mobility. Furthermore, the Miles' invention is concerned with a PCR chip for end-point detection not a Real-Time PCR chip. In addition, there is a problem in that an ionically-labelled probe must be used to detect an amplified PCR product.

SUMMARY OF THE INVENTION

The present invention provides a method for detecting a polymerase chain reaction (PCR) product by measuring an electrical signal in a PCR solution.

According to an aspect of the present invention, there is provided a method for detecting a PCR product, comprising: (a) providing at least a pair of electrodes in a PCR solution-containing vessel; (b) performing PCR; (c) producing an electric field between the electrodes; and (d) measuring a change in a dielectric property in the PCR solution.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

According to the present invention, in step (a), the PCR reaction solution-containing vessel includes, but is not limited to, a conventional bulk PCR tube and a polymerization microchamber. The electrodes are installed to be opposite to each other in the PCR reaction vessel. In the case of the bulk PCR tube, the electrodes are installed to be opposite to each other at a predetermined height from bottom of the tube. Meanwhile, in the case of the polymerization microchamber, the electrodes are installed at the upper and lower sides or the left and right sides of the microchamber, such a way as to be opposite to each other. The electrodes can be formed by conventional methods such as photolithography. Various metal electrodes such as a copper (Cu) electrode, a chromium (Cr)-gold (Au) electrode, and an arsenic (As)-doped silicon electrode may be used as the above electrodes.

In the PCR reaction of step (b), except for PCR reactants and solution, a specifically labelled probe or primer for generating an electrical signal is not required. Therefore, there is no need to use an ionically-labelled primer, unlike the Miles' patent. According to the present invention, a PCR product can be detected without using a specifically labelled probe or primer for generating an electrical signal, but is not limited thereto.

In step (c), an electric field is produced by a conventional alternating current (AC) or direct current (DC) generator, which is connected to the pair of electrodes. Preferably, an AC frequency is in the range from 1 Hz to 100 MHz and an average AC voltage (Vrms) is in the range from 1 mV to 10 V.

In step (d), the dielectric property includes, but is not limited to, an impedance, a dielectric loss, a dielectric constant, and an admittance, which are derived from an electric field. These electrical coefficients can be measured by dielectric property measuring means, which is connected to the electrodes. For example, an impedance sensor operatively connected to the electrodes may be used.

Hereinafter, the present invention will be described more specifically by way of examples. However, the following examples are provided only for illustrations, and thus, the present invention is not limited to or by them.

EXAMPLES

Example 1

Preparation of PCR Tube Provided with Electrodes

Holes were made in a conventional PCR tube and electrodes were inserted in the middle portions of a PCR solution through the holes. Then, while connecting the electrodes to PCR equipment and then performing PCR, an electrical signal was detected immediately after each PCR cycle. In this Example 1, the impedance of amplified DNA was measured.

Figure 1:
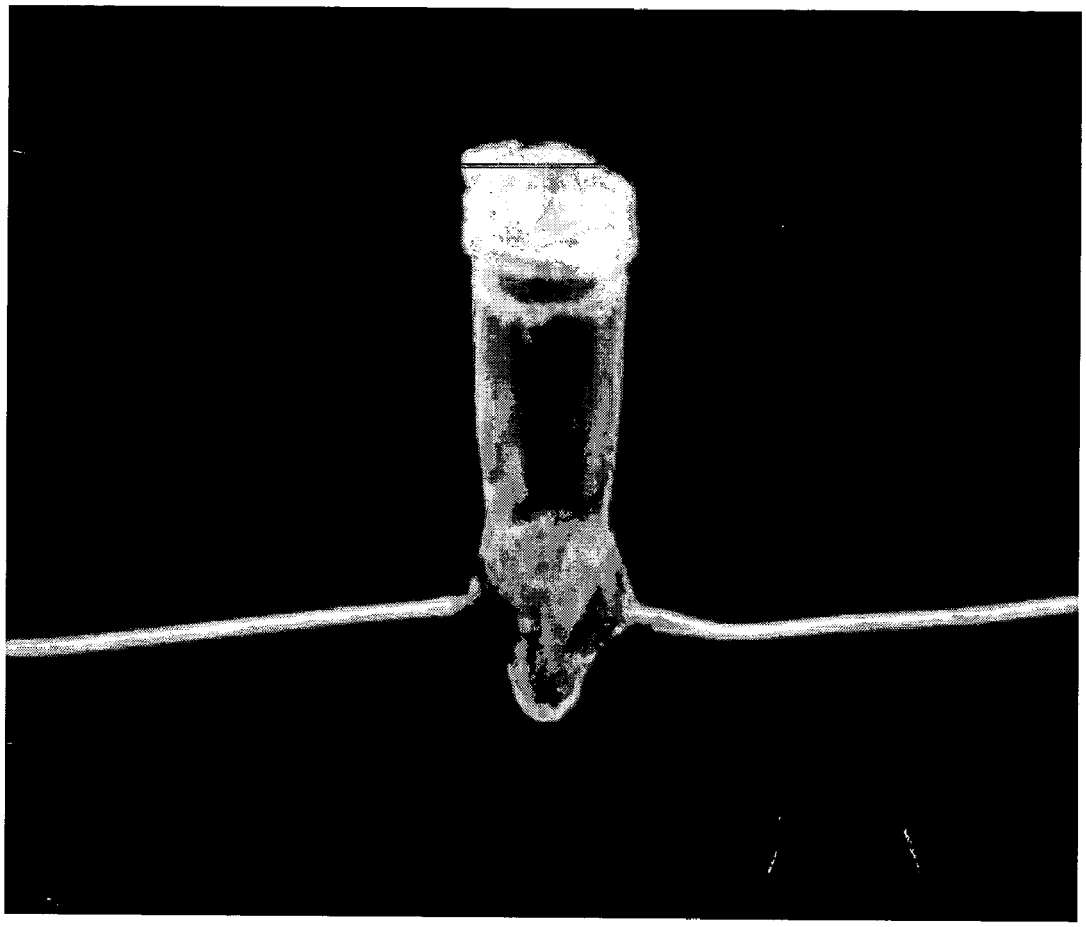
FIG. 1 is a view of a PCR tube provided with electrodes.

In detail, holes with a diameter of 0.3 mm were made at both sides of a 0.2 ml PCR tube at the point spaced 5 mm apart from the bottom of the tube. Then, wires with a diameter of 0.32 mm were inserted into the holes and were used as electrodes. The electrodes are Teflon insulated, silver coated copper wires. The electrodes were fixed at the walls of the tube using a hot epoxy to maintain the distance between the electrodes to 1.5 mm. In order to decrease the surface areas of the electrodes, the diameter of the lower portion of the tube in which the PCR solution was present was maintained to about 1.5 mm and a small-sized electrode was installed at the wall surface in the tube (FIG. 1). Therefore, adsorption of an enzyme or PCR components, which may occur in the surfaces of the electrodes, can be reduced, thereby increasing the detection sensitivity and the product yield.

Example 2

Figure 6:
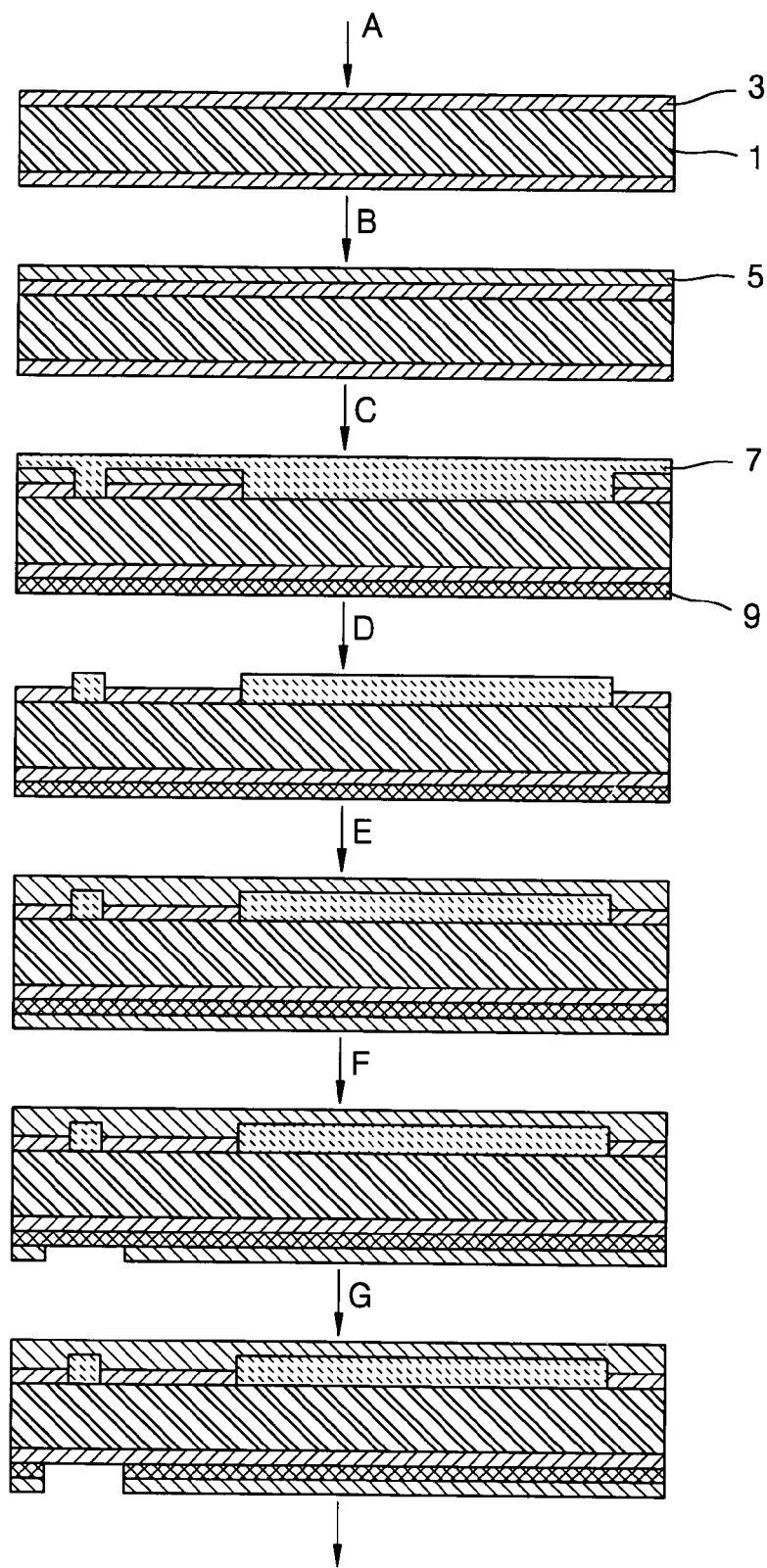
FIGS. 6 and 7 are views of a process of manufacturing a polymerization chamber and electrodes of the PCR chip of FIG. 2.
Figure 7:
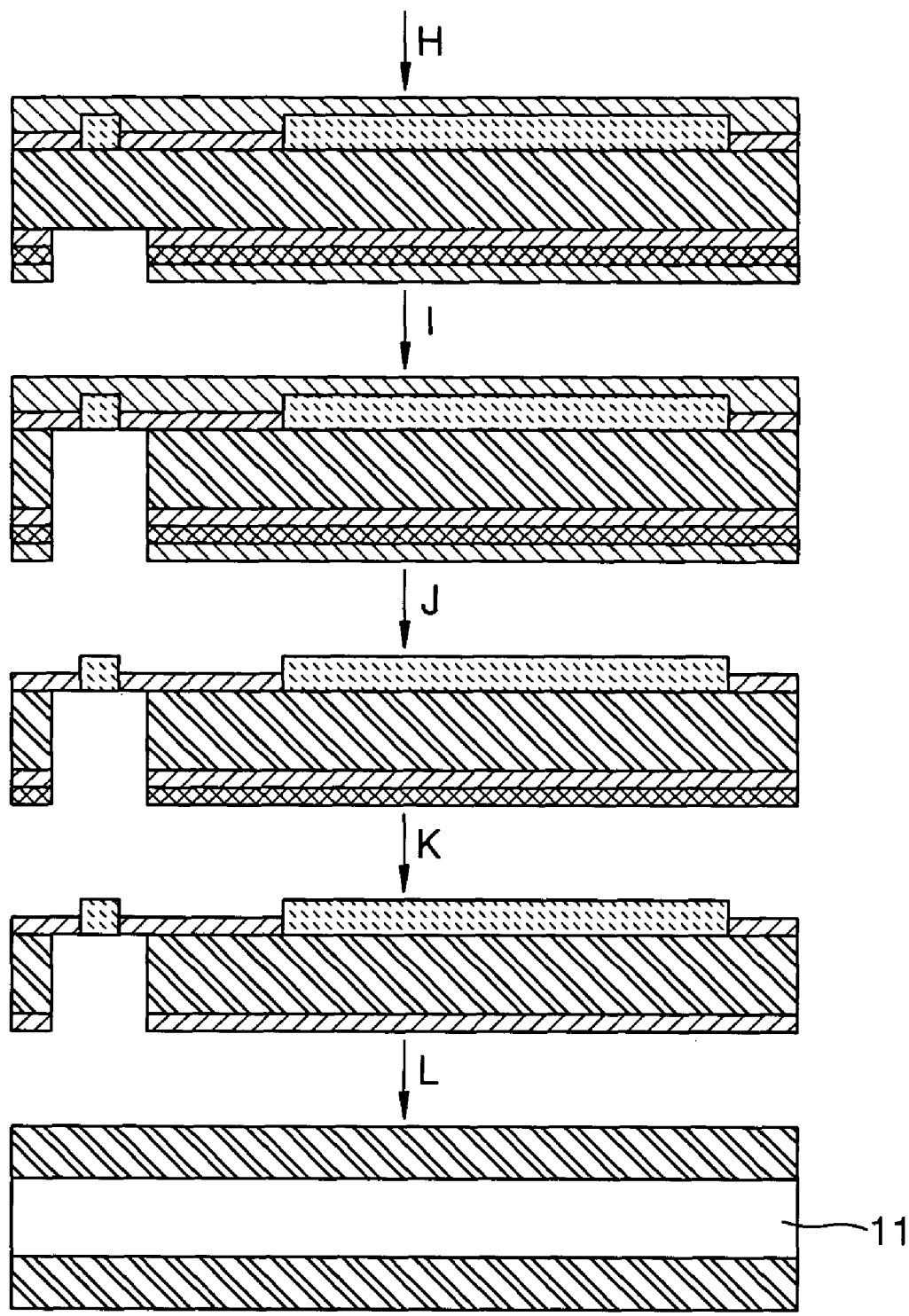

Preparation of PCR Chip with Three-layered Structure having Upper and Lower Electrodes in Chamber A PCR chip having upper and lower electrodes in a chamber was prepared according to the process shown in FIGS. 6 and 7.

First, about 5,000 Å or more thick $SiO_2$ layers 3 were formed on the upper and lower surfaces of an As-doped, n-type silicon wafer 1 using thermal oxidation (step A). The $SiO_2$ layer 3 on the upper surface of the wafer 1 was coated with a photoresist (AZ 5214) 5 (step B). After patterning the upper and lower electrodes on the photoresist using photolithography, the wafer was placed in an etching solution (HF) to thereby remove a patterned $SiO_2$ layer. A film 7 made of Cr and Au was deposited on the upper surface of the exposed wafer and the photoresist using e-beam or sputtering and an Al film 9 was deposited on the lower surface of the wafer (step C). A Au-electrode was formed on the upper electrode by a lift-off process (step D). After coating the Al film 9 with a photoresist and photoresist patterning on the Al film 9 (step E), the Al film 9 was etched and then the $SiO_2$ layer 3 and the silicon wafer 1 were sequentially dry-etched using ICP-RIE (steps F, G, H, and I). After the etching, a remnant photoresist was dissolved using acetone and a remnant Al film was etched (steps J and K).

The upper and lower electrodes formed silicon wafer 1 was anodically bonded to a glass wafer 11, which was formed with holes for a reaction chamber in a PCR chip by a sand blasting process. The bonded wafers were diced to produce a final chip. An anodic bonding is a process which bonds a silicon wafer to a glass wafer. During the anodic bonding, a high electric field and heat allow the migration of positive ions (for example, $Na^+$ ion) of the glass wafer away from the wafers' interface, thereby creating hydrogen bonding between the silicon wafer and the glass wafer.

The upper and lower electrodes prepared in an opposing electrode pattern according to this example are opposite to each other in a three dimensional manner, unlike conventional electrodes, which are formed at a definite position on a two dimensional plane. Therefore, all DNA amplified by PCR can be detected in a chamber.

Figure 2:
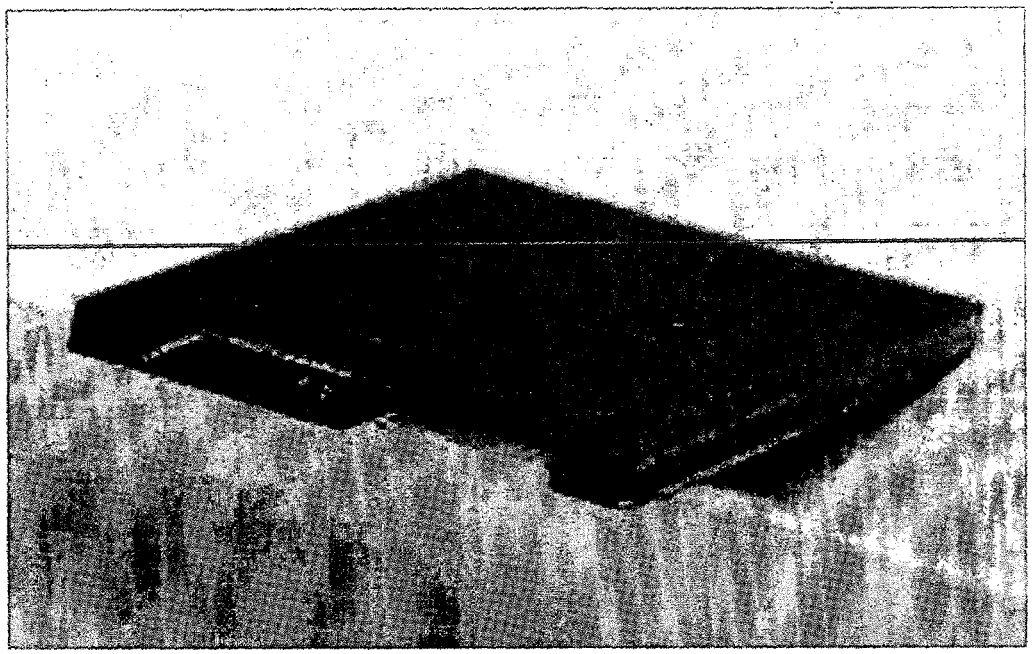
FIG. 2 is a view of an example of a PCR chip containing a PCR chamber provided with electrodes.
Figure 3:
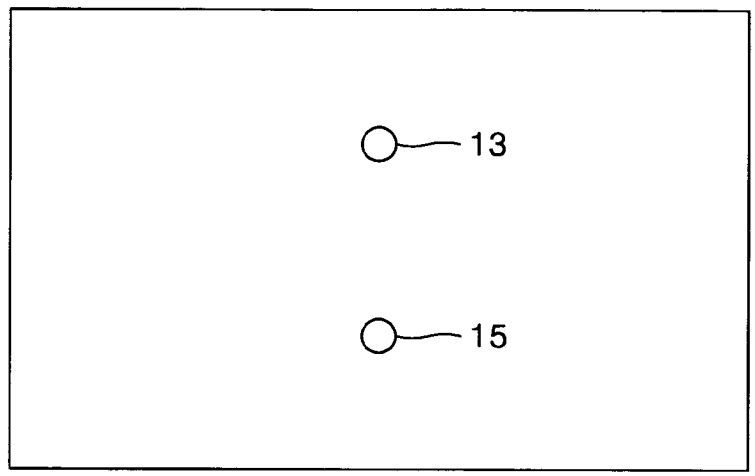
FIGS. 3 through 5 are a plan view, a longitudinal sectional view, and a cross sectional view of the PCR chip of FIG. 2, respectively.
Figure 4:
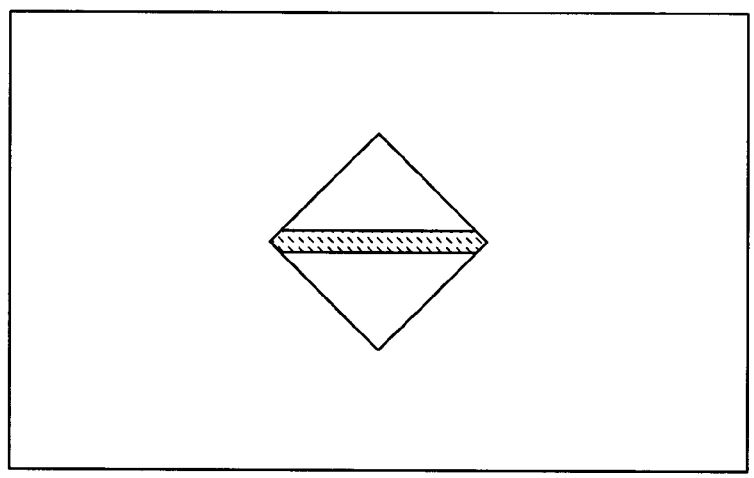
Figure 5:
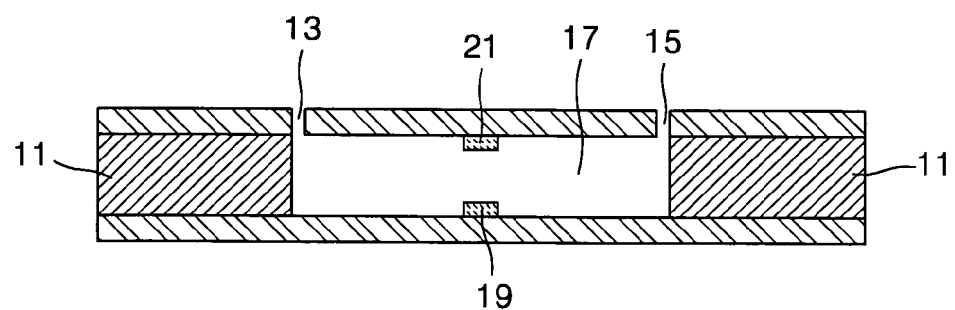

The PCR chip prepared according to this example is shown in FIGS. 2 through 5. FIG. 2 is a perspective view of the PCR chip. FIG. 3 is a plan view of the PCR chip and shows an inlet 13 and an outlet 15. FIG. 4 is a longitudinal sectional view of the PCR chip and shows a polymerization chamber 17 and a lower electrode 19. FIG. 5 is a cross sectional view of the PCR chip and shows the inlet 13, the outlet 15, an upper electrode 21, the lower electrode 19, the polymerization chamber 17, and a glass wafer 11.

Example 3

Preparation of PCR Chip with Two-layered Structure using Silicon Direct Bonding

A PCR chip with a two-layered structure was prepared in the same manner as in Example 2 except that two silicon wafers were directly bonded to each other.

Since a glass wafer was not used in this Example, a production cost and a volume of a chamber could be easily adjusted. According to this method, without using a metal electrode, after etching small areas of $SiO_2$ layers on the upper and lower surfaces of an As-doped, n-type silicone wafer, the etched $SiO_2$ layers were used as electrodes. Therefore, adsorption of biomolecules on a metal surface can be prevented, thereby increasing the yield of a PCR product and the detection sensitivity.

Example 4

Real-time Detection of PCR Product

Real-time detection of a PCR product was performed using PCR equipment comprising a PCR tube provided with electrodes as in Example 1 and an impedance sensor operatively connected to the electrodes.

PCR reaction was performed using plasmid DNA (323 bp) as a template and Tag DNA polymerase. Among the total 35 cycles of PCR, the impedance (resistance) was measured at $1^{st}$, $5^{th}$, $10^{th}$, $15^{th}$, $20^{th}$, $25^{th}$, $30^{th}$, and $35^{th}$ cycle after each of 1 minute extension reaction, respectively. Then, the temperature during the measurement was the same as in the extenison reaction, and an AC voltage of 100 mV, and a frequency of 500 to 5,000 Hz was used during the measurement. As a control, PCR reaction was performed in the absence of a DNA template and then the impedance was measured.

Figure 8:
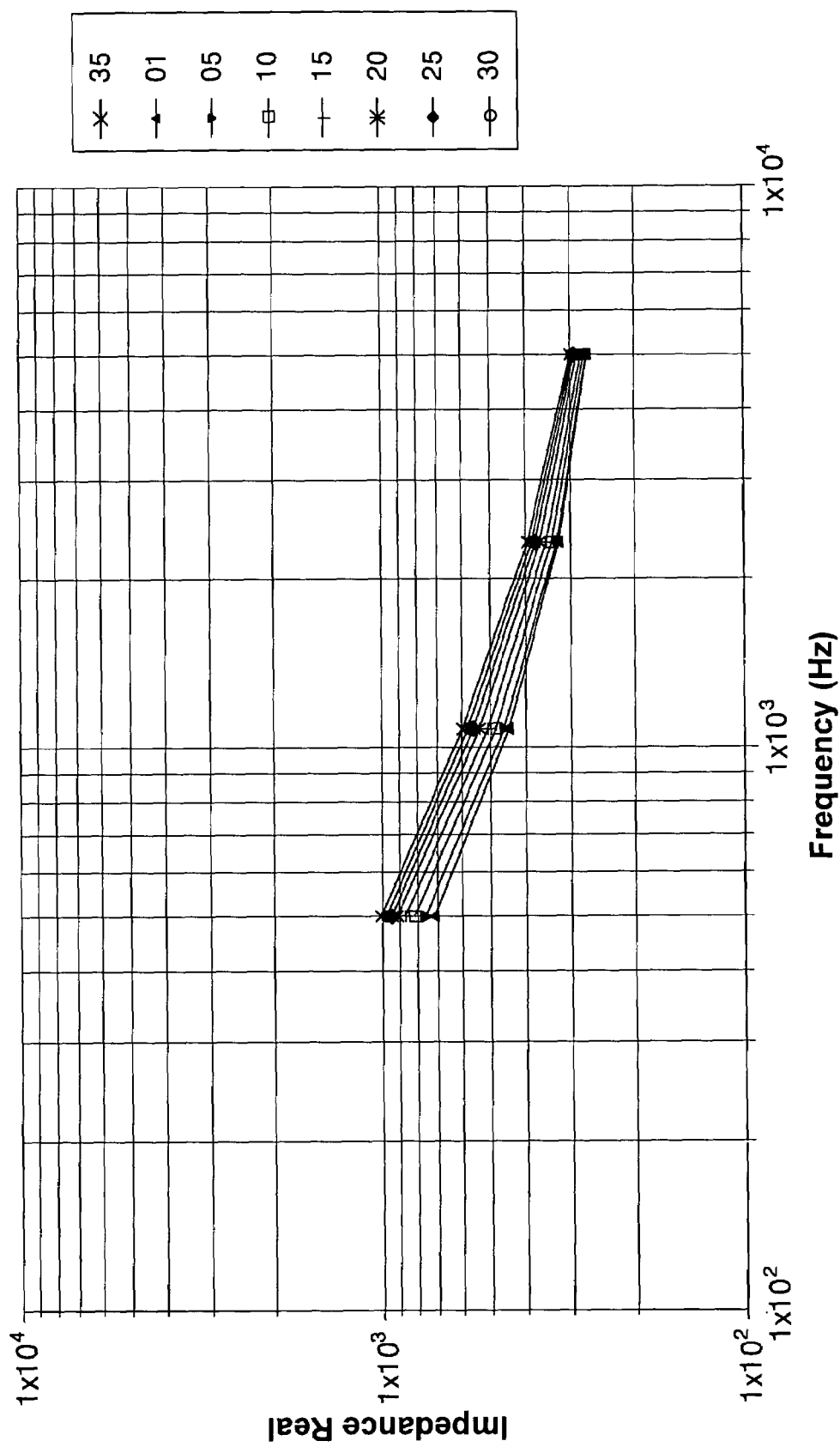
FIG. 8 is a graph of a change in the impedance real part as a function of a frequency in control PCR cycles.

The results are shown in FIGS. 8 through 11. FIG. 8 shows a graph of a change in the impedance real part as a function of a frequency in an increase of control PCR cycles. As shown in FIG. 8, as the number of PCR cycles increases, the impedance real part increases. Also, as a frequency increases, a difference between the impedance real parts in $1^{st}$ cycle and $35^{th}$ cycle decreases.

Figure 9:
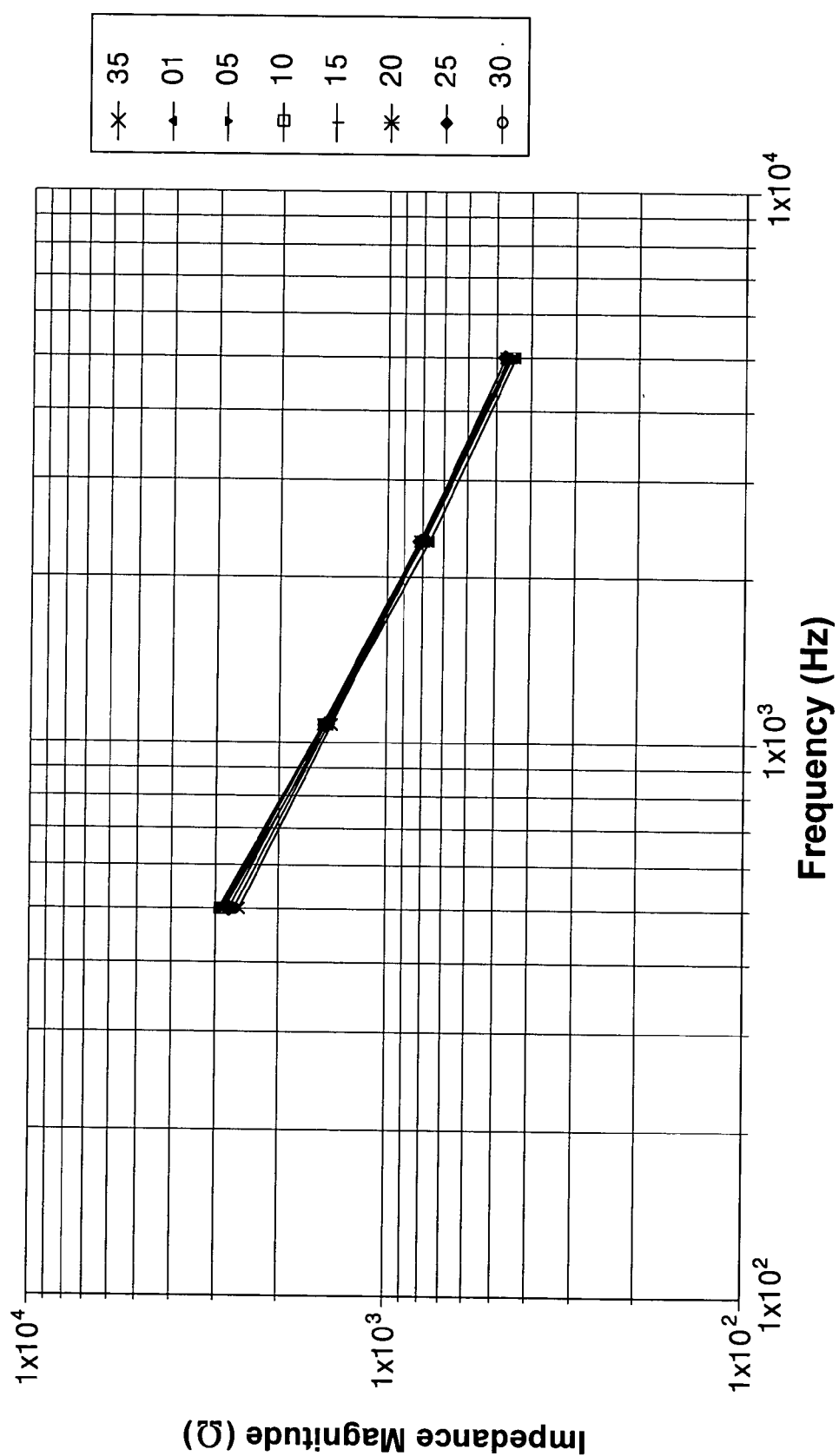
FIG. 9 is a graph of a change in the impedance magnitude as a function of a frequency in control PCR cycles.

FIG. 9 shows a graph of a change in the impedance magnitude as a function of a frequency in control PCR cycles. As shown in FIG. 9, a change in the impedance imaginary part remarkably decreases with increase of the number of the PCR cycles, when compared to changes in the impedance real part, impedance imaginary part, tangent delta, etc. as shown in FIG. 8. Little change in the impedance magnitude with increase of the number of PCR cycles occurred at about 1,000 Hz zone. In spite of no DNA amplification, a difference between the impedance magnitudes in $1^{st}$ cycle and $35^{th}$ cycle at 1,077 Hz was about 45 Ω. This can be explained by adsorption of dNTPs, primer, and enzyme on electrodes and intrinsic interference of the detection system. This difference must be considered at detection values of DNA amplified by PCR.

Figure 10:
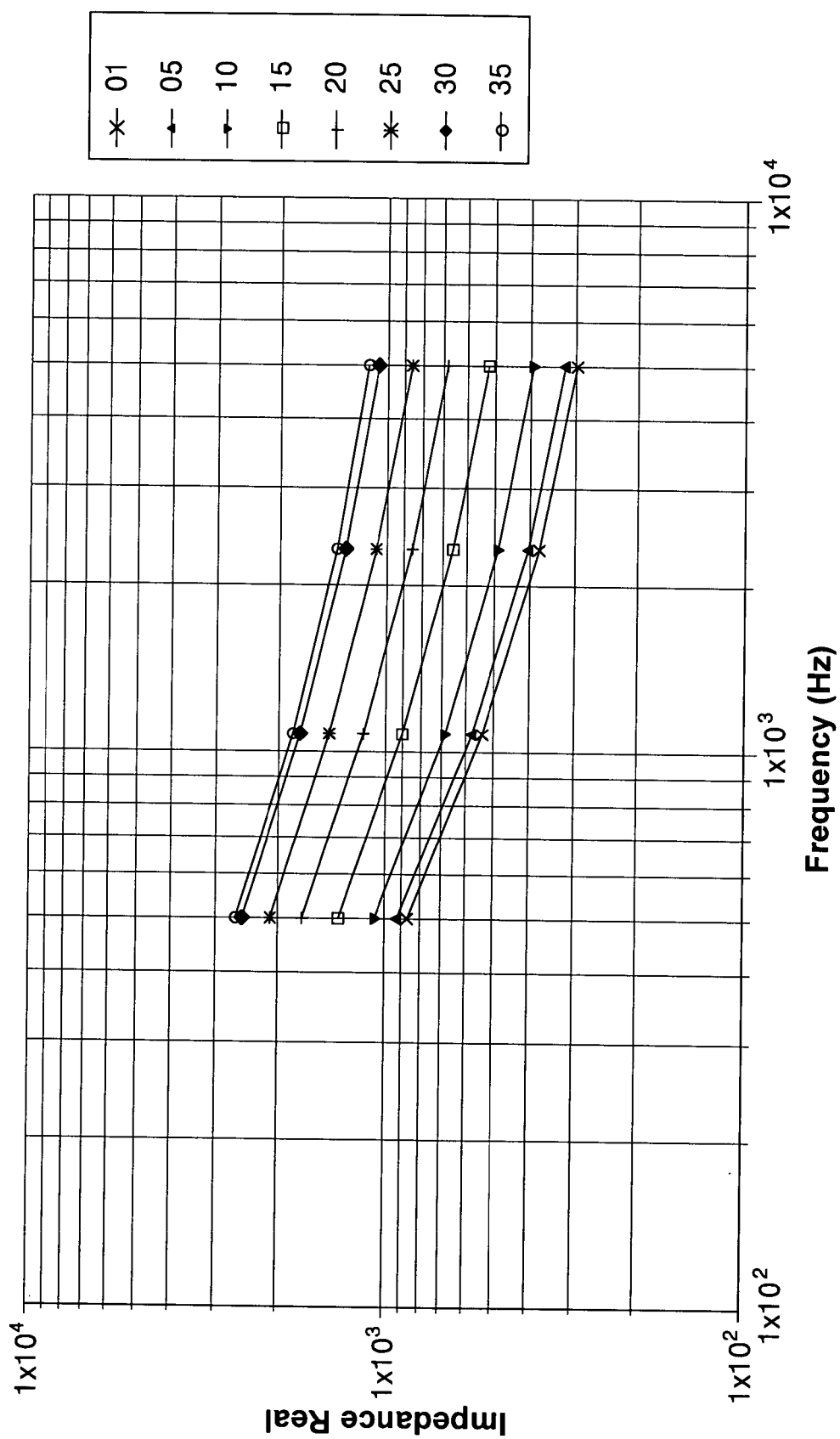
FIG. 10 is a graph of a change in the impedance real part as a function of a frequency in actual PCR cycles.

FIG. 10 shows a graph of a change in the impedance real part as a function of a frequency in actual PCR cycles. As shown in FIG. 10, as the number of PCR cycles increases, the concentration of DNA increases and thus there are considerably differences among the impedance real parts. This corresponds to the theory that when the number of PCR cycles is n, the number of DNA is amplified by $2^n$ times.

Figure 11:
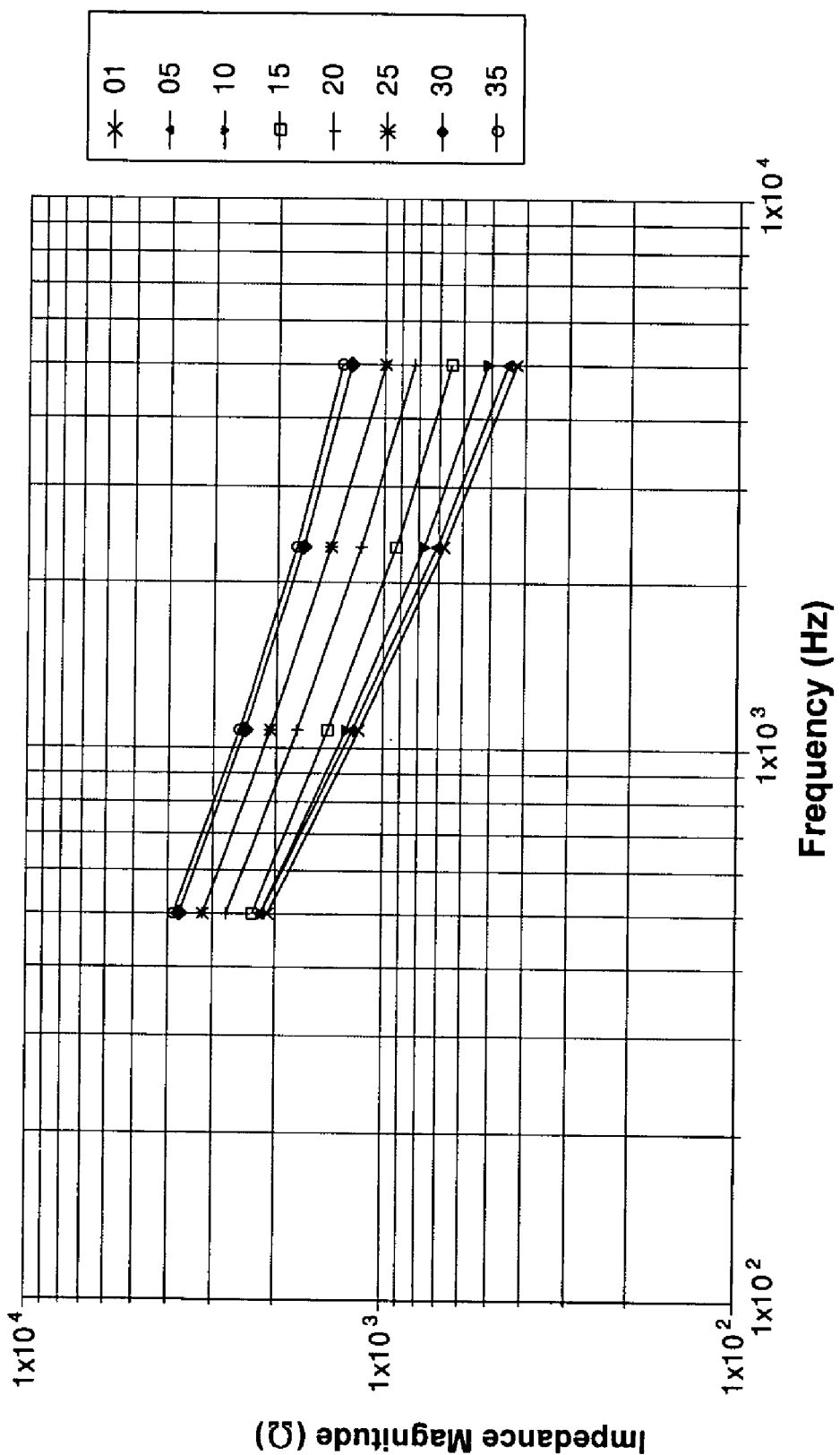
FIG. 11 is a graph of a change in the impedance magnitude as a function of a frequency in actual PCR cycles.

FIG. 11 shows a graph of a change in the impedance magnitude as a function of a frequency in actual PCR cycles. As shown in FIG. 11, as the number of PCR cycles increases, the impedance magnitude remarkably increases. Small change in the impedance magnitudes at $1^{st}$ through $5^{th}$ cycle is explained by the theory that DNA amplification occurs exponentially. Meanwhile, the reason why a change in the impedance magnitudes at $30^{th}$ through $35^{th}$ cycle is small is that PCR reaches a plateau phase due to exhaustion of PCR components.

From the results in FIGS. 8 through 11, it can be seen that the impedance magnitude is most suitable for quantitative assay of a DNA product according to increase of the number of PCR cycles, rather than measured values such as the impedance real and imaginary parts. This is because system interference is the smallest in the impedance magnitude relative to other measured values, as shown in FIGS. 8 and 9.

Example 5

Change in Impedance Magnitude According to PCR Cycles at Specific Frequency

Real-time detection of a PCR product was performed in the same manner as in Example 4 except that a change in the impedance magnitude according PCR cycles at a specific frequency was measured. According to Example 4, the result that most corresponds to the PCR theory revealed at a frequency of about 1,000 Hz. Based on this result, the impedance magnitudes of amplified DNA and non-amplified DNA according to PCR cycles were measured at a frequency of 1,077 Hz. The results are presented in FIGS. 12 and 13.

Figure 12:
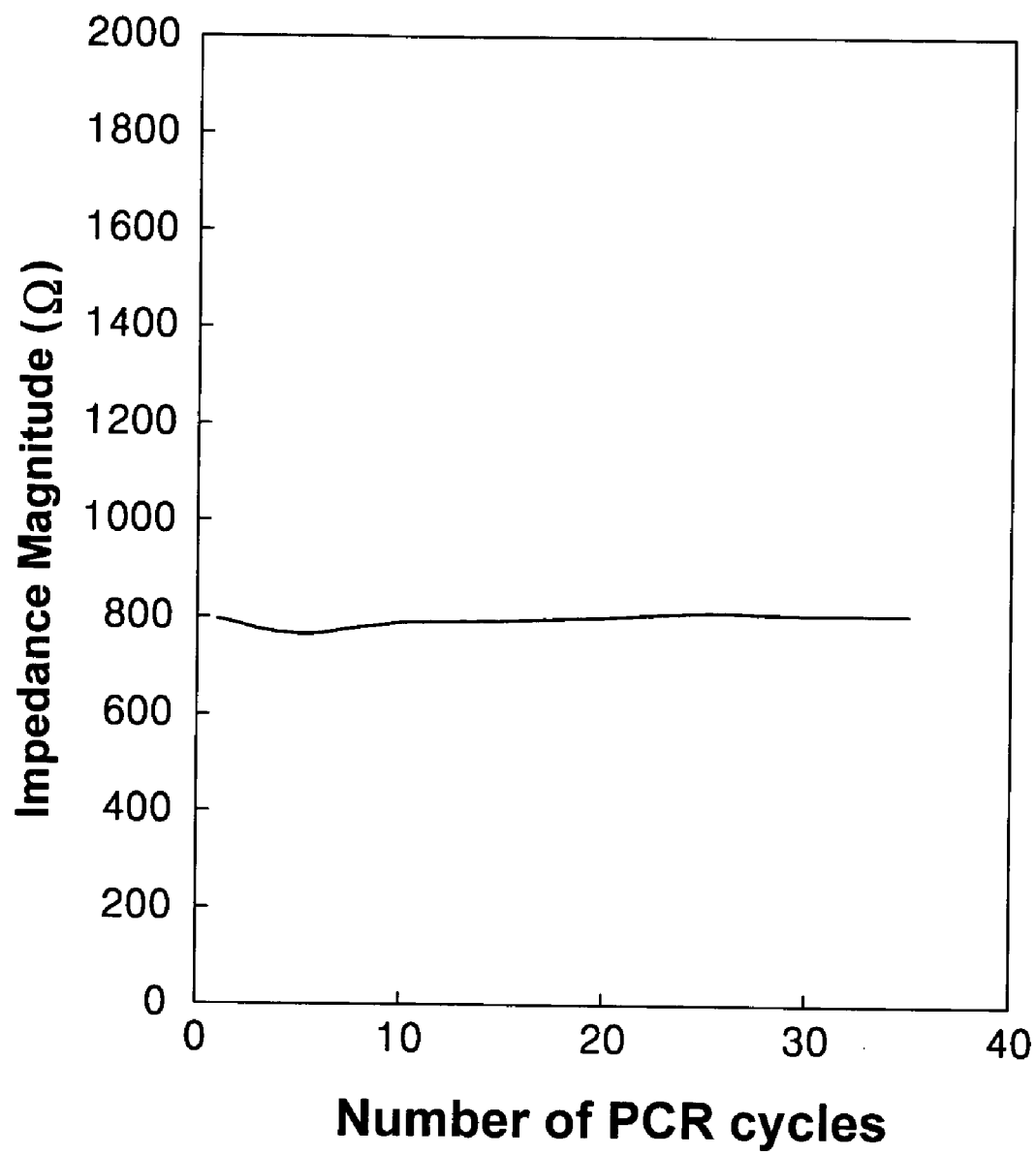
FIG. 12 is a graph of a change in the impedance magnitude in control PCR cycles.
Figure 13:
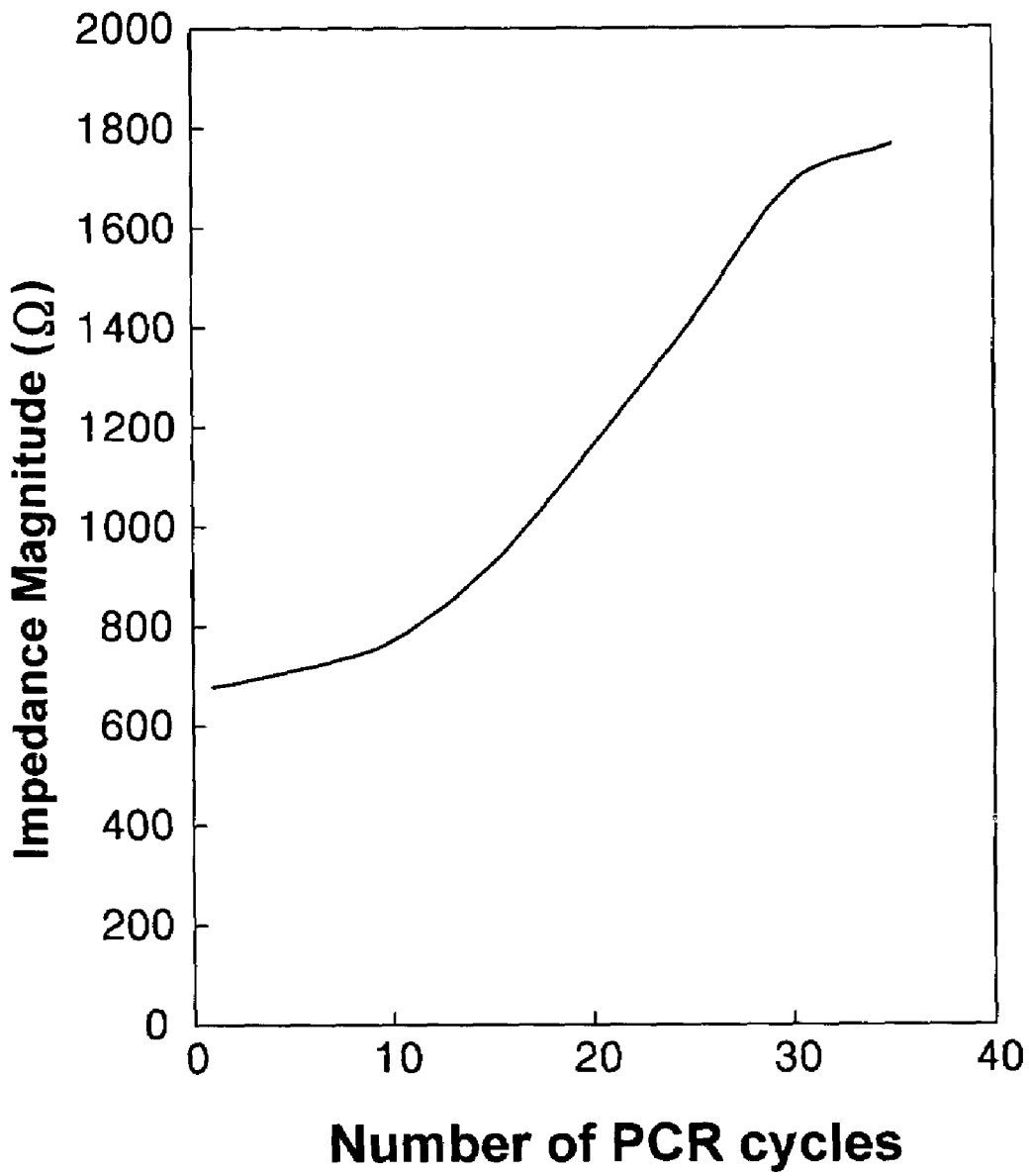
FIG. 13 is a graph of a change in the impedance magnitude in actual PCR cycles.
Figure 14:
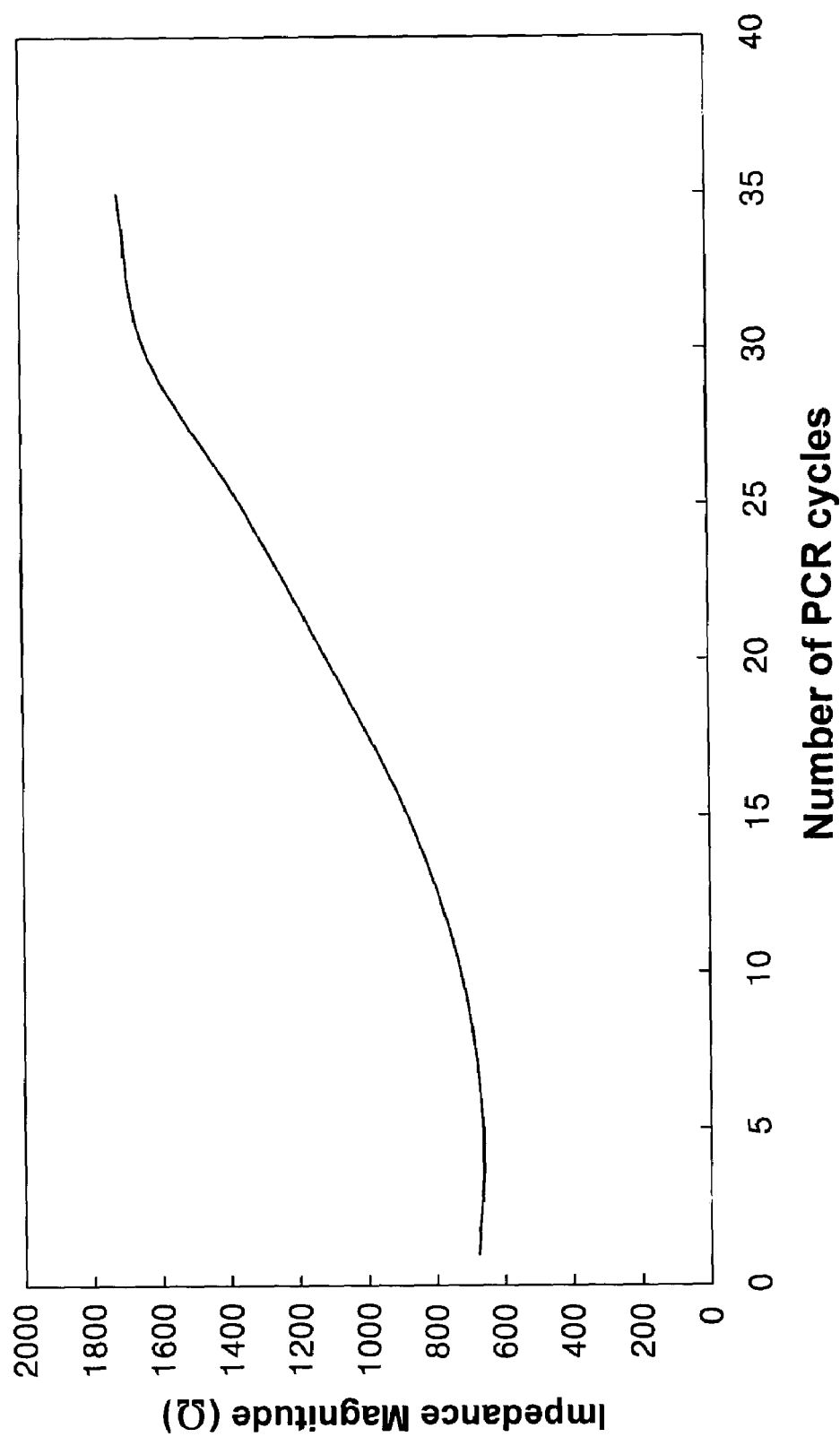
FIG. 14 is a graph of a change in the impedance magnitude in error-corrected, actual PCR cycles.

FIG. 12 shows a graph of a change in the impedance magnitude in a control PCR reaction solution on a real time basis and FIG. 13 shows a graph of a change in the impedance magnitude in actual PCR cycles. The difference between the impedance magnitudes in $1^{st}$ cycle and $35^{th}$ cycle at 1,077 Hz was about 45 Ω, as shown in FIG. 12, like in Example 4. This value is an error caused by intrinsic interference of the detection system. As shown in FIG. 13, a change in the impedance magnitude with increase of the number of PCR cycles forms a S-curve, which represents exponential increase of a PCR product. Based on the above results, the 45 Ω error-corrected impedance magnitude in the actual PCR cycles is shown in FIG. 14.

As apparent from the above description, according to the present invention, a PCR product can be measured in real time during a PCR process.

Furthermore, a detection system can be miniaturized by detection of an electrical signal.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for detecting a polymerase chain reaction (PCR) product, comprising
    providing at least a pair of electrodes in a PCR solution-containing vessel, wherein the pair of electrodes is connected to an impedance sensor;
    performing PCR;
    producing an electric field between the pair of electrodes; and
    measuring a change in impedance magnitude of the PCR solution,
    wherein the measuring is performed in the absence of an additional probe for generating an electrical signal and at a predetermined alternating current voltage frequency with an increase in the number of PCR cycles.

2. The method according to claim 1, wherein the predetermined alternating current voltage frequency is about 1,000 Hz.

* * * * *